(12) United States Patent
Lenkman et al.

(10) Patent No.: US 9,296,405 B2
(45) Date of Patent: Mar. 29, 2016

(54) MEDICAL EQUIPMENT CART HAVING A ROTARY ATTACHMENT

(71) Applicant: Sightpath Medical, LLC, Bloomington, MN (US)

(72) Inventors: Thomas Lenkman, Saint Charles, MO (US); David Massey, Saint Charles, MO (US)

(73) Assignee: Sightpath Medical, LLC, Bloomington, MN (US)

( * ) Notice: Subject to any disclaimer, the term of this patent is extended or adjusted under 35 U.S.C. 154(b) by 69 days.

(21) Appl. No.: 14/289,226

(22) Filed: May 28, 2014

(65) Prior Publication Data

US 2015/0344051 A1   Dec. 3, 2015

(51) Int. Cl.
*B62B 3/02* (2006.01)
*B62B 5/04* (2006.01)
*B62B 5/00* (2006.01)

(52) U.S. Cl.
CPC ... *B62B 3/02* (2013.01); *B62B 5/00* (2013.01); *B62B 5/049* (2013.01)

(58) Field of Classification Search
CPC ............ B62B 3/02; B62B 5/00; B62B 5/049; B62B 2203/07; B62B 2203/071; B62B 2203/60
USPC ........ 280/47.34, 47.35, 79.11, 79.2; 414/672, 414/665, 669, 792.2
See application file for complete search history.

(56) References Cited

U.S. PATENT DOCUMENTS

| | | |
|---|---|---|
| 1,499,530 A | 7/1924 | Henderson |
| 1,804,542 A | 5/1931 | Perin |
| 2,172,154 A | 9/1939 | Perin |
| 2,783,899 A | 3/1957 | Gutridge |
| 3,125,035 A | 3/1964 | Loomis |
| 3,190,473 A | 6/1965 | Loef |
| 3,296,981 A | 1/1967 | Bergstrand |
| 3,451,656 A | 6/1969 | Goodacre |
| 3,527,470 A | 9/1970 | Ord |
| 3,829,063 A * | 8/1974 | Holzworth ............ B62B 3/0618 254/2 R |
| 4,237,794 A | 12/1980 | Biaggini et al. |
| 4,457,551 A | 7/1984 | Anthony |
| 4,746,262 A | 5/1988 | Anderson |
| 4,755,089 A | 7/1988 | Ellgass |
| 4,755,099 A | 7/1988 | Belveal |
| 5,018,931 A | 5/1991 | Uttley |
| 5,032,045 A | 7/1991 | Calco |
| 5,542,500 A * | 8/1996 | Emrey ...................... B62B 3/04 187/244 |
| 5,782,602 A | 7/1998 | Mehta et al. |

(Continued)

*Primary Examiner* — John Walters
(74) *Attorney, Agent, or Firm* — Husch Blackwell LLP

(57) ABSTRACT

A cart for transporting and securing ophthalmological lasers and other highly sensitive equipment to medical facilities by a vehicle, and within medical facilities by rolling the cart is disclosed. The cart includes a cart base member with a mounting plate attached to the top portion of the cart base member, a locking mechanism attached to the mounting plate, and a circular plate, rotary swivel bearing and roller plate contained between the cart base member and the mounting plate. The circular plate allows the mounting plate and the equipment mounted thereon to rotate when the locking mechanism is in its unlatched position. This rotation allows the equipment, which may include asymmetrical equipment such as an overhanging arm associated therewith, to rotate enough to allow the otherwise asymmetrical equipment to fit through a doorway and accordingly be transported from one room in a clinic or other surgical site to another room.

13 Claims, 7 Drawing Sheets

(56) References Cited

U.S. PATENT DOCUMENTS

| | | |
|---|---|---|
| 5,845,914 A | 12/1998 | Lenkman |
| 6,099,220 A | 8/2000 | Poth |
| 6,537,017 B2 * | 3/2003 | Stone .................. B65G 1/07 187/269 |
| 7,153,081 B2 | 12/2006 | Watanabe |
| 7,556,270 B2 | 7/2009 | Friedman |
| 7,736,104 B2 | 6/2010 | Hobson |
| 8,151,787 B1 * | 4/2012 | Sivert .................. F24J 2/38 126/608 |
| 2012/0068395 A1 * | 3/2012 | Daeschner .............. B23P 19/00 259/55 |
| 2013/0121802 A1 * | 5/2013 | Albrecht ................ H01L 21/68 414/809 |

* cited by examiner

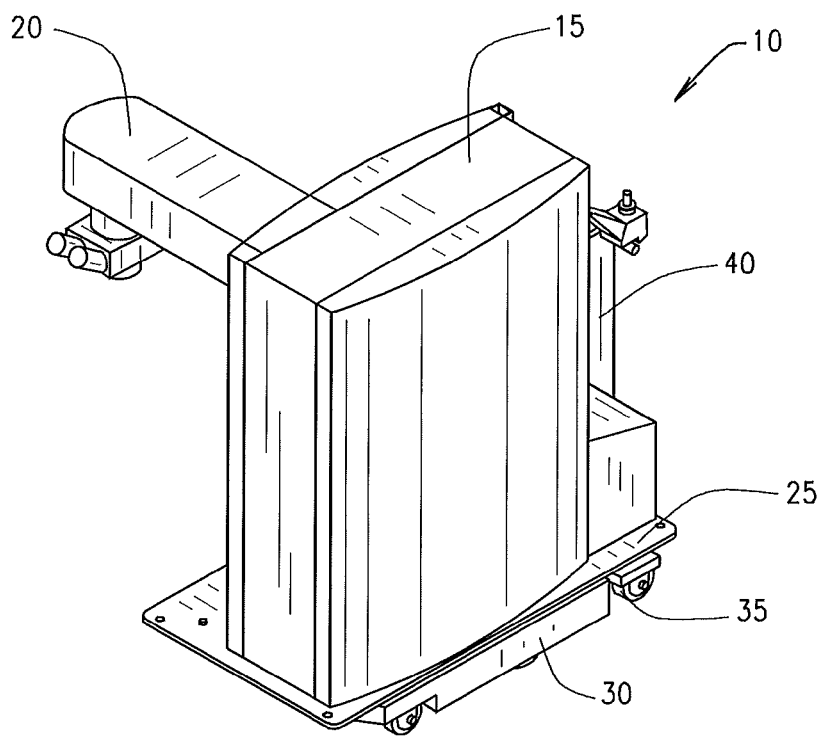
F I G . 1
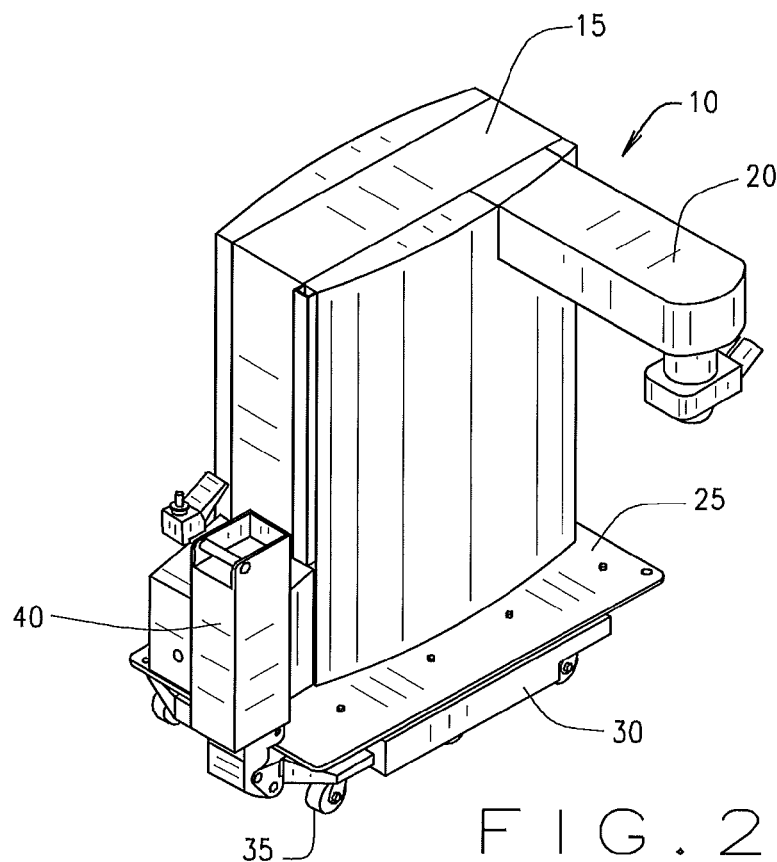
F I G . 2

MEDICAL EQUIPMENT CART HAVING A ROTARY ATTACHMENT

BACKGROUND OF INVENTION

The present invention relates to a portable cart for transporting highly sensitive equipment, such as a laser used in ophthalmological surgeries. The cart includes the ability to be secured in a truck or other vehicle for transport to various locations and subsequent removal of the portable cart with the ophthalmic laser for delivery to a doctor's office or clinic to use and operate the laser as desired.

Lasers have been used increasingly in a variety of ophthalmological surgeries. One of their most well-known uses is in LASIK surgeries for correcting myopia, hypermetropia, and astigmatism. The lasers used in the aforementioned procedures are large and can be quite heavy. Often the laser used in a LASIK surgery is an excimer laser. The excimer lasers and associated equipment may be particularly large and heavy.

Many such ophthalmic lasers are asymmetrical in addition to being large and heavy. The asymmetry is largely attributed to an overhanging arm that is used during ophthalmic surgeries and placed above an operating space, often a patient bed. The overhanging arm is usually placed above a patient's eye during a procedure because the arm may include the incision laser itself. The overhanging arm is a necessary component of the device, but it presents some logistical challenges.

Ophthalmic lasers and their associated equipment are expensive. As such, clinics and other surgery sites often include only one laser for performing the aforementioned surgeries. The equipment is often transported to the site disassembled, before being assembled on site. The equipment is usually assembled on site because the lasers including the overhanging arm and associated equipment is difficult to maneuver through a facility. Specifically, the lasers and associated equipment may not be able to fit through doorways such that they may be moved from one room to another within a facility. This often is principally due to the overhanging arm extending from the laser equipment, and the asymmetry resulting therefrom. Therefore, because the surgery sites often only have one such laser, the lasers are confined to one room as a result of their difficulty in being maneuvered.

Because the lasers and their associated equipment are particularly sensitive, self-contained portable carts for transporting the aforementioned ophthalmological lasers and associated sensitive equipment such as that shown in U.S. Pat. No. 5,845,914 ("the '914 patent") were developed. Such portable carts are able to securely and safely transport highly sensitive equipment such as ophthalmological lasers from one location to another using an air cushion suspension system. Air cushions contained in a mobile cart act as shock absorbers for when the cart and its highly sensitive equipment are in transit. Multiple carts securing highly sensitive equipment may be secured within a truck trailer or other transportation means. The cart may be removably mounted to the floor of the truck cab to prevent the cart and highly sensitive equipment from jostling therein and damaging the equipment during transportation.

The cart from the prior art '914 patent includes a mechanism for locking the cart down in a truck cab where the cart is housed and transported from one location to another. In the prior art reference, the mechanism is driven by a power activated retractable arm or pin that engages a floor support of the truck floor. While the power activated mechanism eliminates the requirement of manually releasing the retractable arm from the support, in the event of a power failure, unloading the carts from a truck cab can become difficult without damaging a cart, floor support, retractable arm, or the truck cab floor.

A solution that alleviates some of the aforementioned issues involving ophthalmological lasers and their associated equipment is desired. More particularly, a solution that allows the laser and associated equipment to fit through doorways such that it may be moved from room to room within a facility is desired. Moreover, a solution that provides a manual release within a truck cab is desired so as to provide a means for unloading equipment in the event of a power failure.

SUMMARY OF INVENTION

The present invention relates to a medical equipment cart that includes a rotating mechanism allowing a base portion of the cart to rotate, thus causing an arm associated with the highly sensitive medical equipment to also rotate. This rotation allows the cart to be maneuverable through a doorway such that it may be transported within a clinic or other surgical site.

In the present invention, a cart base member including a drive system known in the art is used to cushion and transport the ophthalmological laser and associated equipment. A mounting plate for receiving and securing the laser and associated equipment is secured to and above the cart base member. The laser and associated equipment is mounted to and above the cart base member. A locking mechanism, such as a control handle, is also mounted to the cart base member. The control handle may be used to secure a number of electrical and other control components therein, and it may further be used to help secure the laser and associated equipment in place.

The present invention further includes a circular plate which is attached at its bottom portion to the cart base member via a rotary swivel bearing. At its upper portion, the circular plate is attached with the mounting plate, which is still placed above and attached to the cart base member in the invention. The circular plate is surrounded and received by a roller plate that includes rollers for facilitating the rotating motion of the mounting plate. When the locking mechanism has been disengaged from the laser and associated equipment, the rotary plate allows the mounting plate and its laser equipment mounted thereon to rotate. The swiveling action causes the position of the overhanging arm of the laser equipment relative to the cart base member to also rotate. As a result of the re-positioning of the overhanging arm, the overhanging arm may be sufficiently positioned so as to allow the equipment and its arm to go through a doorway such that the equipment may be moved from one room to another within a clinic or other surgery site.

A support frame member mounted to a truck cab floor or other surface further secures the cart and equipment by receiving a power activated retractable arm or pin associated with the cart base member. The power activated retractable arm or pin of the present invention further comprises a manual release lever for quickly releasing the pin from the support frame member such that the cart and equipment may be removed from the truck cab floor or other surface in the event of a power failure.

BRIEF DESCRIPTION OF DRAWINGS

FIG. 1 illustrates a perspective view of one embodiment of an ophthalmological laser and its associated equipment mounted to a mounting plate which is further mounted to a cart base member, the laser and its equipment constructed and assembled according to the teachings of the present invention.

FIG. 2 illustrates a perspective view of the laser and equipment of FIG. 1, further illustrating a control handle of the present invention in a latched position.

DETAILED DESCRIPTION

Figure 3:
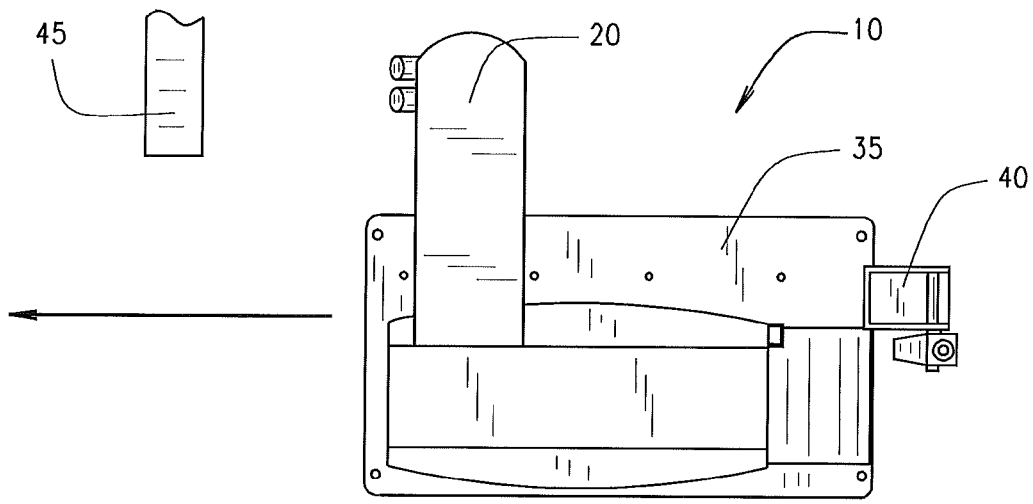
FIG. 3 illustrates a top plan view of the laser and equipment of FIG. 2 as it appears approaching a doorway.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention.

As explained above, the cart of the present invention is designed for use with an ophthalmological laser and other highly sensitive equipment that is able to securely and stably transport the laser or other highly sensitive equipment in a truck cab or other transportation vehicle and in transit within a clinic or surgical site. Moreover, the cart described herein may be used with a plurality of laser or highly sensitive equipment types. The method in which the present invention operates and is constructed will become apparent from the description that follows.

Referring to the drawings more particularly by reference numbers, wherein like numerals refer to like parts, the number 10 in FIG. 1 identifies a cart for securing and transporting ophthalmological lasers and associated equipment constructed according to the teachings of the present invention. The cart 10 illustrated in FIG. 1 is for transporting ophthalmological medical device 15, though using cart 10 to transport highly sensitive medical equipment other than device 15 is further contemplated herein. Device 15 includes an overhanging arm portion 20 which may be used to perform various procedures for which the device 15 is used. The device 15 may be mounted to a mounting plate 25 associated with a powered drive cart base member 30. The mounting plate 25 is positioned and located to receive and secure device 15.

Mounting plate 25 is releasably secured to the upper surface of cart base member 30 via a plurality of bolts with a plurality of components described in detail therebetween, though other attachment means such as a screw mechanism, latch mechanism or other methods known or foreseeable in the art are contemplated herein. The mounting plate 25 should not be mounted so substantially such that it cannot rotate, however. Cart base member 30 includes wheels 35 for facilitating the movement of the cart base member 30 and its associated device 15 across a floor surface.

The cart base member 30 preferably includes a number of components known in the art including air cushions for absorbing shock and keeping device 15 or other highly sensitive equipment secure and reducing the damage caused by jostling during transportation. The cart base member further preferably includes a locking mechanism, such as control handle 40 shown in FIG. 2, which serves, at least in part, to secure mounting plate 25 in place when in a locked position. Upon release of the locking mechanism, mounting plate 25 may be rotated as described in greater detail herein below. As shown in FIG. 2, control handle 40 may be attached at its bottom portion to cart base member 30 via a hinged connection. Control handle 40 may further be releasably attached to cart base member 30 at its side portion in a manner that will be described in greater detail herein below.

FIG. 3 illustrates the cart 10 and associated device 15 approaching a standard doorway 45, for example a 36 inch wide doorway. As illustrated in FIG. 3, the overhanging arm 20 prevents the cart 10 and device 15 from passing through doorway 45 when cart 10 is in an unrotated position. Overhanging arm 20 causes the cart 10 and device 15 to be too wide to fit through doorway 45. As such, the present invention includes a means for rotating the mounting plate 25 and thus device 15 and repositioning the overhanging arm 20 such that the overhanging arm 20 may fit through doorway 45.

Figure 4:
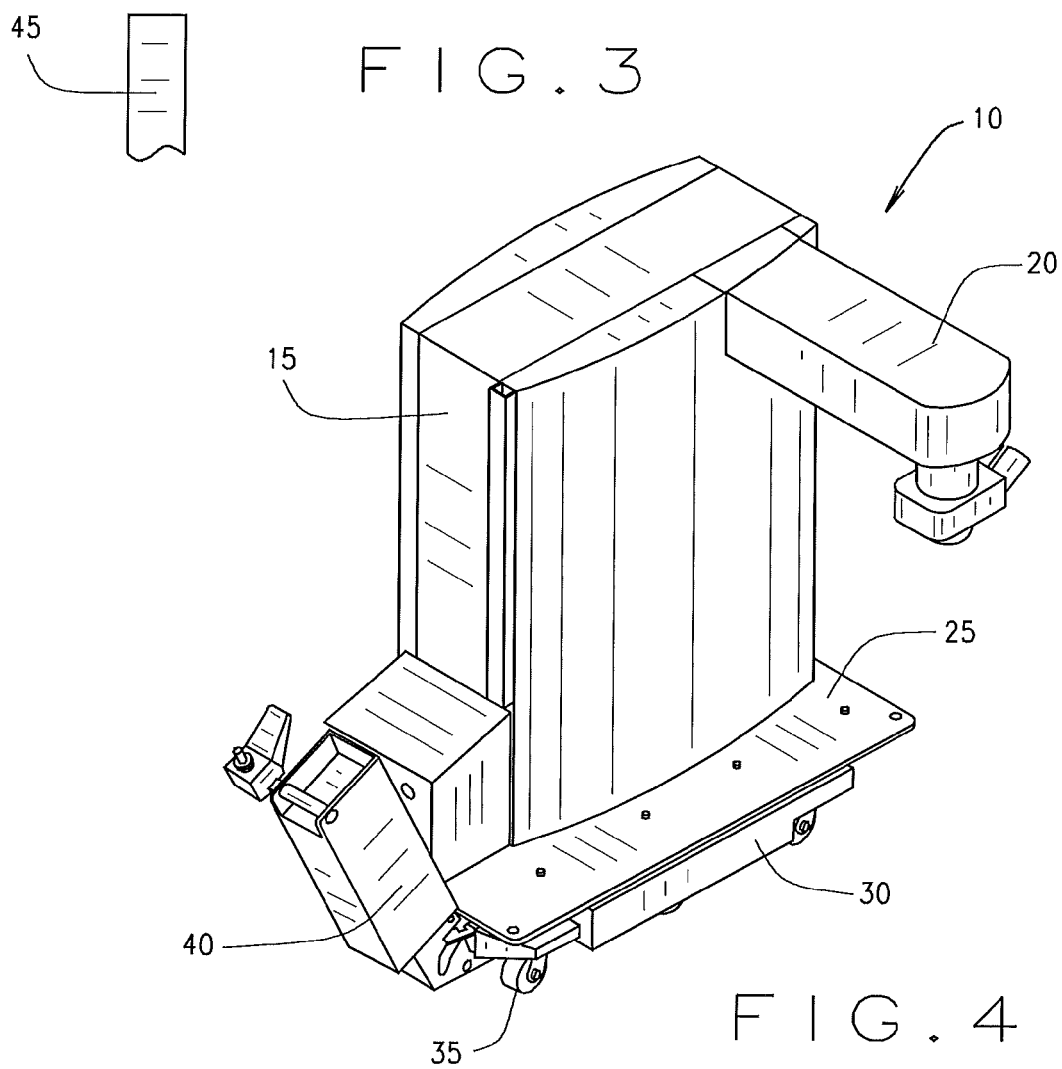
FIG. 4 illustrates a perspective view of the laser and equipment of FIG. 2, wherein the control handle of the present invention is in an unlatched position.
Figure 5:
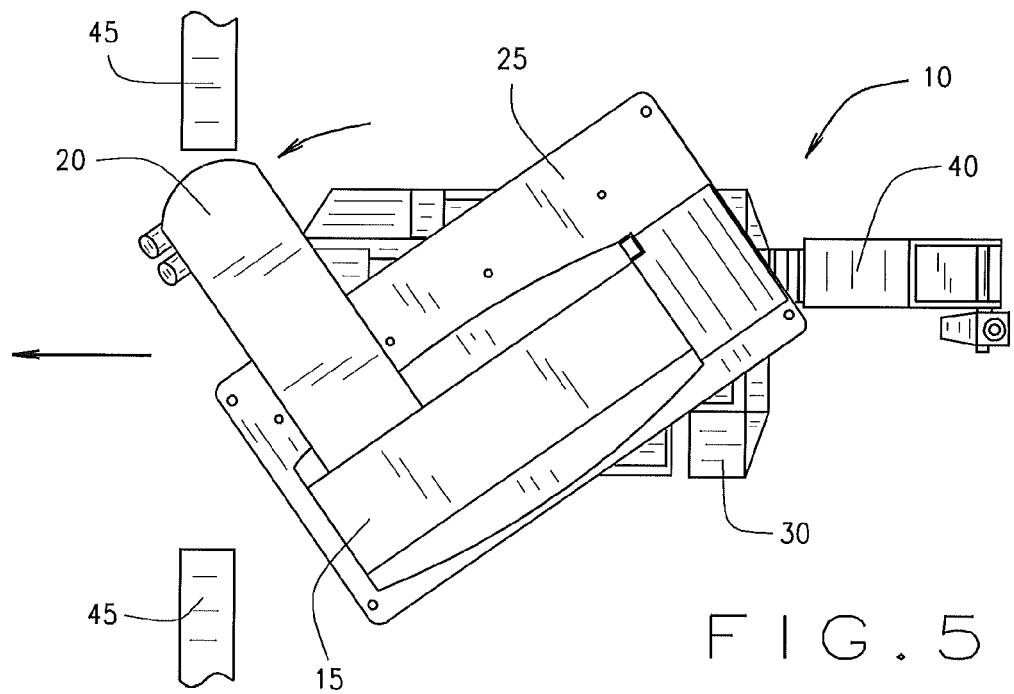
FIG. 5 illustrates a top plan view of the laser and equipment of FIG. 4 in a rotated position as it appears entering a doorway.
Figure 6:
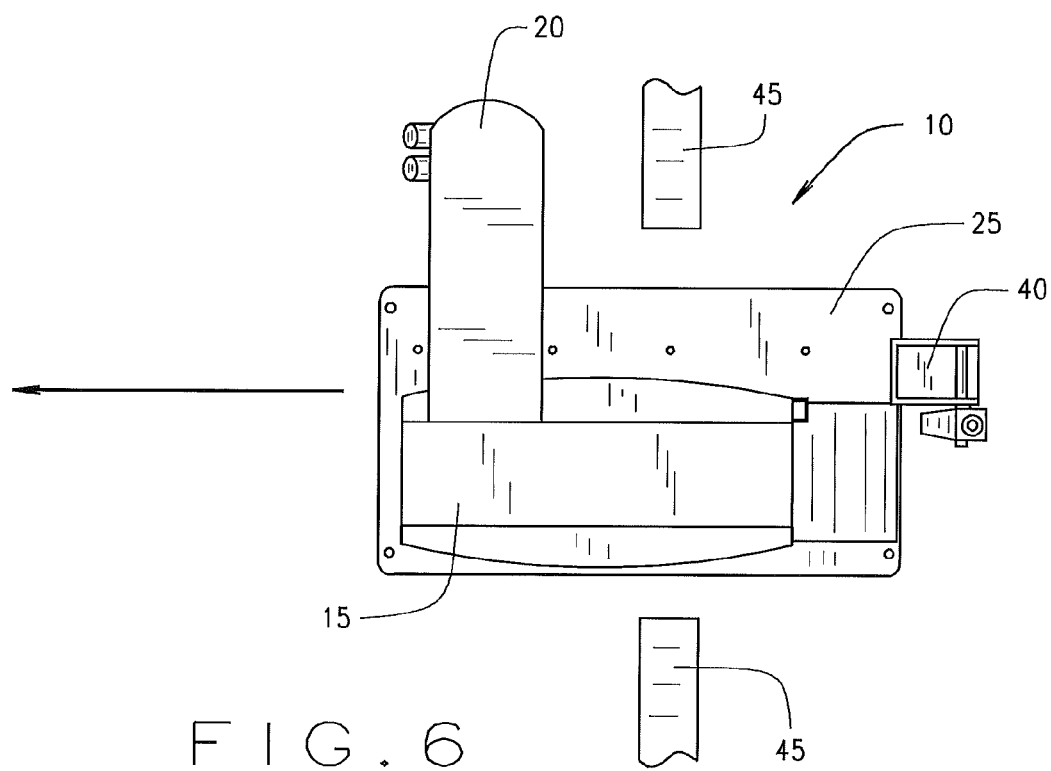
FIG. 6 illustrates a top plan view of the laser and equipment of FIG. 5 as it appears after having gone through a doorway and returned to its non-rotated position.

In operation, control handle 40 serves as a locking mechanism to secure the mounting plate 25 in place. Control handle 40 may be released from mounting plate 25 in a manner described in greater detail below. As a result of the release of the control handle 40, mounting plate 25 and consequently device 15 and overhanging arm 20 are able to rotate. FIG. 4 shows control handle 40 released from mounting plate 25, allowing the mounting plate 25 and associated equipment to swivel, as illustrated in FIG. 5. When mounting plate 25 swivels, as illustrated in FIG. 5, the positioning of the overhanging arm 20 sufficiently rotates to allow overhanging arm 20 to clear doorway 45. Once the arm 20 has passed through the doorway 45, the mounting plate 25 may be rotated to return to being positioned and located above cart base member 30. Control handle 40 may then be returned to its locked position and reengaged with mounting plate 25 as illustrated in FIG. 6. Alternative to the control handle 40 illustrated in FIGS. 2 and 4, a person of ordinary skill in the art would recognize that other known locking mechanisms or combinations of elements could serve as a means for securing the mounting plate 25.

Figure 7:
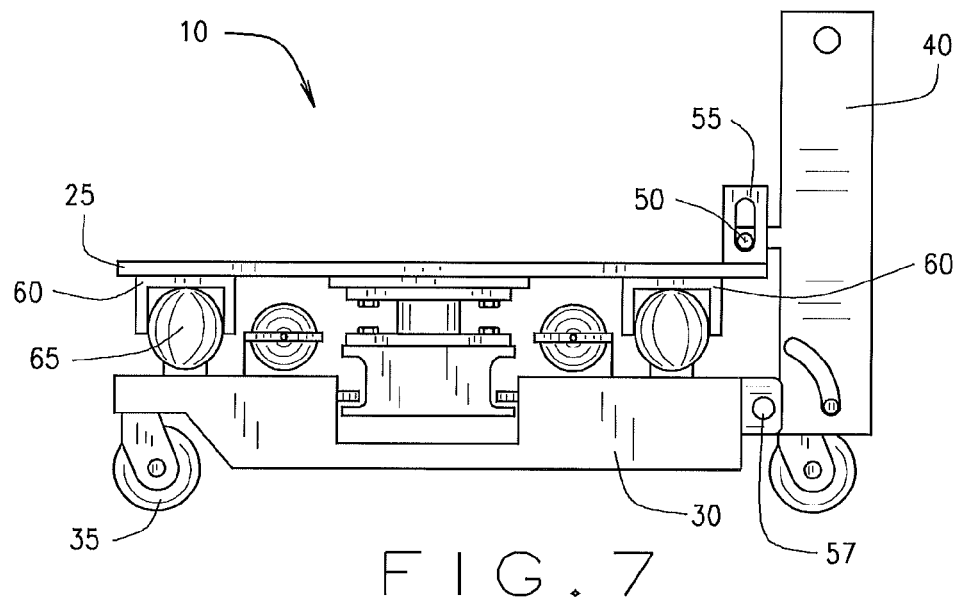
FIG. 7 illustrates a sectional elevation view of the cart base member of the present invention in its locked position.

FIG. 7 illustrates a cross-section of the cart 10 when it is in its locked position (i.e., when it is unable to rotate). In the locked position, control handle 40 is releasably attached to mounting plate 25. In the illustrated embodiment, the control handle 40 includes a barrel bolt lock 50 as commonly known in the art. The barrel bolt 50 is received by and is releasably connected to mounting plate 25 via mounting bracket 55. Other means for releasably securing control handle 40 to mounting plate 25 are herein contemplated, for example a friction fit mechanism, a latch, a screw device, or other semi-permanent attachment means known or foreseeable in the art.

Control handle 40 may be attached to cart base member 30 at its bottom portion via a hinged connection such as hinge 57.

Control handle 40 may include therein a number of components for operating the cart 10. For example, control handle 40 may include electronics for allowing an operator to move the cart 10 electronically. Such electronics may allow the cart 10 to be moved via a joystick which is in electrical and/or data communication with powered drive cart base member 30 via electronics contained within the control handle 40. Control handle 40 may further contain a pneumatic system for modulating the shock absorbing mechanism discussed herein, as well as batteries for powering cart 10.

When the control handle 40 is in its locked position, mounting plate 25 is unable to swivel because it is abutting control handle 40. In the illustrated embodiment, mounting plate 25 is further abutting air bladder containers 60 which contain air bladders 65 therein. The air bladders 65 may help to reduce the impact on the highly sensitive equipment such as device 15 associated with the cart 10. In the preferred embodiment, cart 10 includes four air bladders 65. The two air bladders 65 illustrated in FIG. 7 are illustrative of the positions at which the air bladders 65 are placed longitudinally on the cart 10. In FIG. 7, air bladders 65 are inflated. The remaining two air bladders 65 of the present invention are in substantial alignment with the air bladders 65 illustrated such that the positioning of all four air bladders 65 forms a rectangular shape. The air bladder containers 60 may extend across the latitudinal or transverse portion of cart 10; therefore each container 60 may contain the two air bladders 65 in substantial alignment with one another therein.

Figure 8:
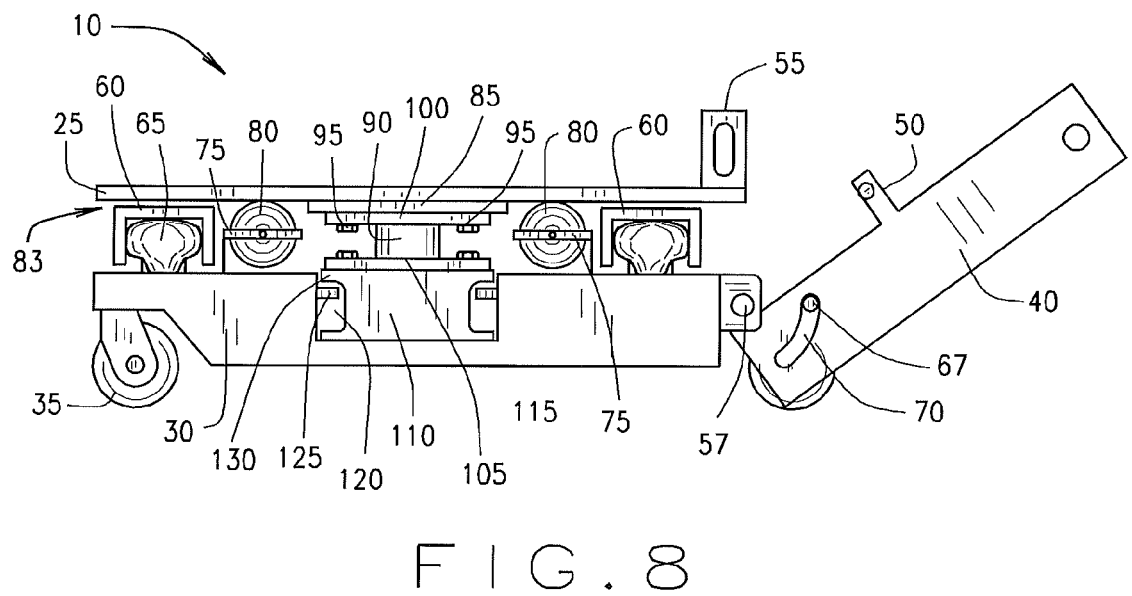
FIG. 8 illustrates a sectional elevation view of the cart base member of FIG. 7 in its unlocked position.

In operation, to unlock the cart, and prepare mounting plate 25 for rotation, control handle 40 should be released from mounting plate 25. By removing barrel bolt 50 from bracket 55, the control handle 40 may be pulled rearwardly such that its upper portion is removed from contact with mounting plate 25, as illustrated in FIG. 8. As the control handle 40 is pulled rearwardly, a transverse ledge 67 associated with and contained within a curved slot 70 keeps the lower portion of control handle 40 attached to the cart base member 30. The hinge 57 may further keep the control handle 40 and cart base member 30 attached. Other means for keeping the control handle 40 and cart base member 30 known or foreseeable in the art are herein contemplated.

In addition to the control handle 40 being leaned rearwardly from the mounting plate 25, air bladders 65 should be deflated in order to prepare mounting plate 25 for rotation. The air bladders 65 may be deflated via a pneumatic mechanism contained within control handle 40. When the air bladders 65 are deflated, containers 60 are no longer pushed upwardly by bladders 65, thus resulting in containers 60 moving downwardly toward the floor. When the containers 60 are pushed downwardly, the mounting plate 25 also descends downwardly. The mounting plate 25 descends downwardly until it abuts a roller plate 75 contained therein. The roller plate 75 (illustrated in FIG. 9) includes a plurality of rollers 80 for facilitating the rotation of mounting plate 25. When the mounting plate 25 has descended in the aforementioned process, a gap 83 exists between the containers 60 and mounting plate 25 such that the mounting plate 25 may rotate without interference from containers 60.

When the mounting plate 25 descends downwardly, circular plate 85, which is attached at its top surface to mounting plate 25 further descends. Circular plate 85 is attached at its lower surface to rotary swivel bearing 90. Bolts 95 may be used to attach an upper plate 100 of rotary swivel bearing 90 with circular plate 85 and circular plate 85 with mounting plate 25. Rotary swivel bearing 90 (illustrated in FIG. 10) may include upper plate 100 and lower plate 105, wherein plates 100 and 105 are capable of rotating independently of one another. Thus when mounting plate 25 is rotated, the rotary swivel bearing 90 functionally rotates the mounting plate 25 by upper plate 100 which is mounted to mounting plate 25, while lower plate 105 remains attached at its bottom portion to a slotted block 110. In an alternative embodiment, lower plate 105 may be attached to a rotating mechanism, and lower plate 105 rotates in order to cause upper plate 100 to further rotate. Slotted block 110 may be contained within a cavity 115 of cart base member 30. Slotted block 110 includes slots 120 (more clearly illustrated in FIG. 10) that receive and contain therein lips 125 associated with cart base member 30. Other means for retaining lower plate 105 to allow upper plate 100 to independently rotate are contemplated.

When the air bladders 65 are inflated as illustrated in FIG. 7, the lips 125 abut overhanging portion 130 of slotted block 110 to prevent the entire assembly from being ejected from the cart base member 30. When the bladders 65 are deflated, the lips 125 abut lower portion 135 of slotted block 110.

Thus, in operation, when the air bladders 65 are inflated as illustrated in FIG. 7, mounting plate 25 may not be rotated. Yet when the air bladders 65 are deflated, as illustrated in FIG. 8, the mounting plate 25 is ready to be rotated in the manner illustrated in FIG. 5.

Figure 9:
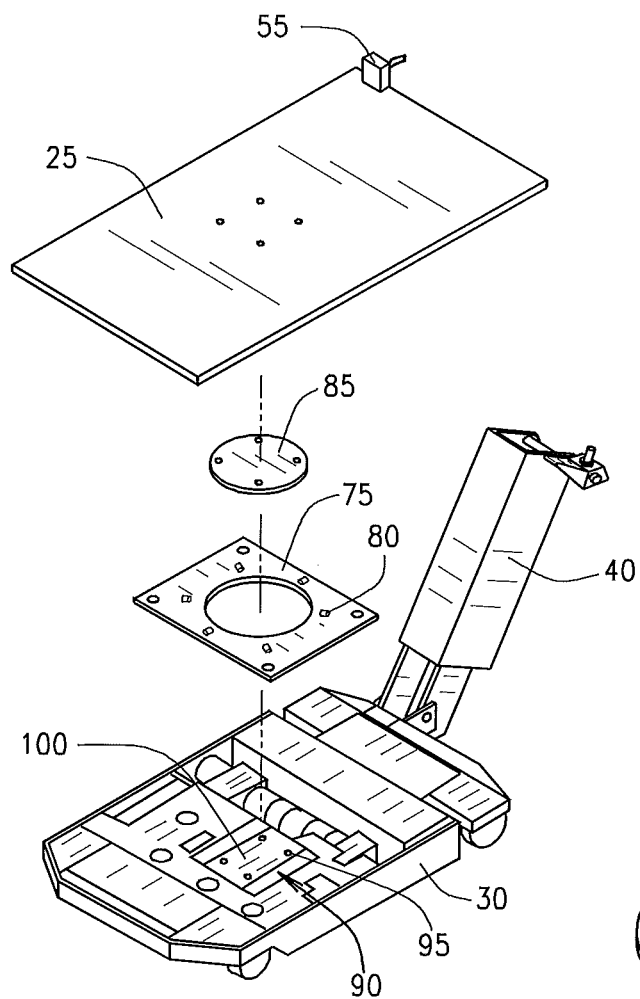
FIG. 9 illustrates an exploded perspective view of various components associated with the cart base member of FIGS. 7 and 8.
Figure 10:
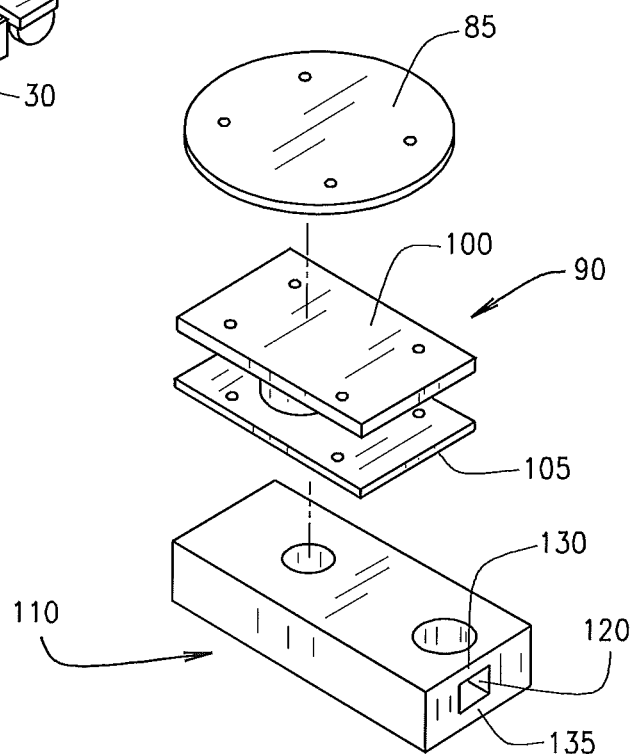
FIG. 10 illustrates an exploded perspective view of various components associated with the cart base member of FIGS. 7, 8, and 9.

FIGS. 9 and 10 further illustrate some of the components described herein above. FIG. 9 illustrates cart base member 30 having received and containing rotary swivel bearing 90. Roller plate 75, including rollers 80 for facilitating the rotation of mounting plate 25, is further illustrated. Rollers 80 may be of varying sizes, as illustrated in FIGS. 7-9. Other means of facilitating the rotation of mounting plate 25 such as a frictionless surface or a track system are contemplated herein. As illustrated in FIG. 9, roller plate 75 may be sized and positioned for receiving circular plate 85. FIG. 10 illustrates slotted block 110 including slot 120 (its corresponding slot in substantial alignment is not illustrated) and portions 130, 135 thereof.

Figure 11:
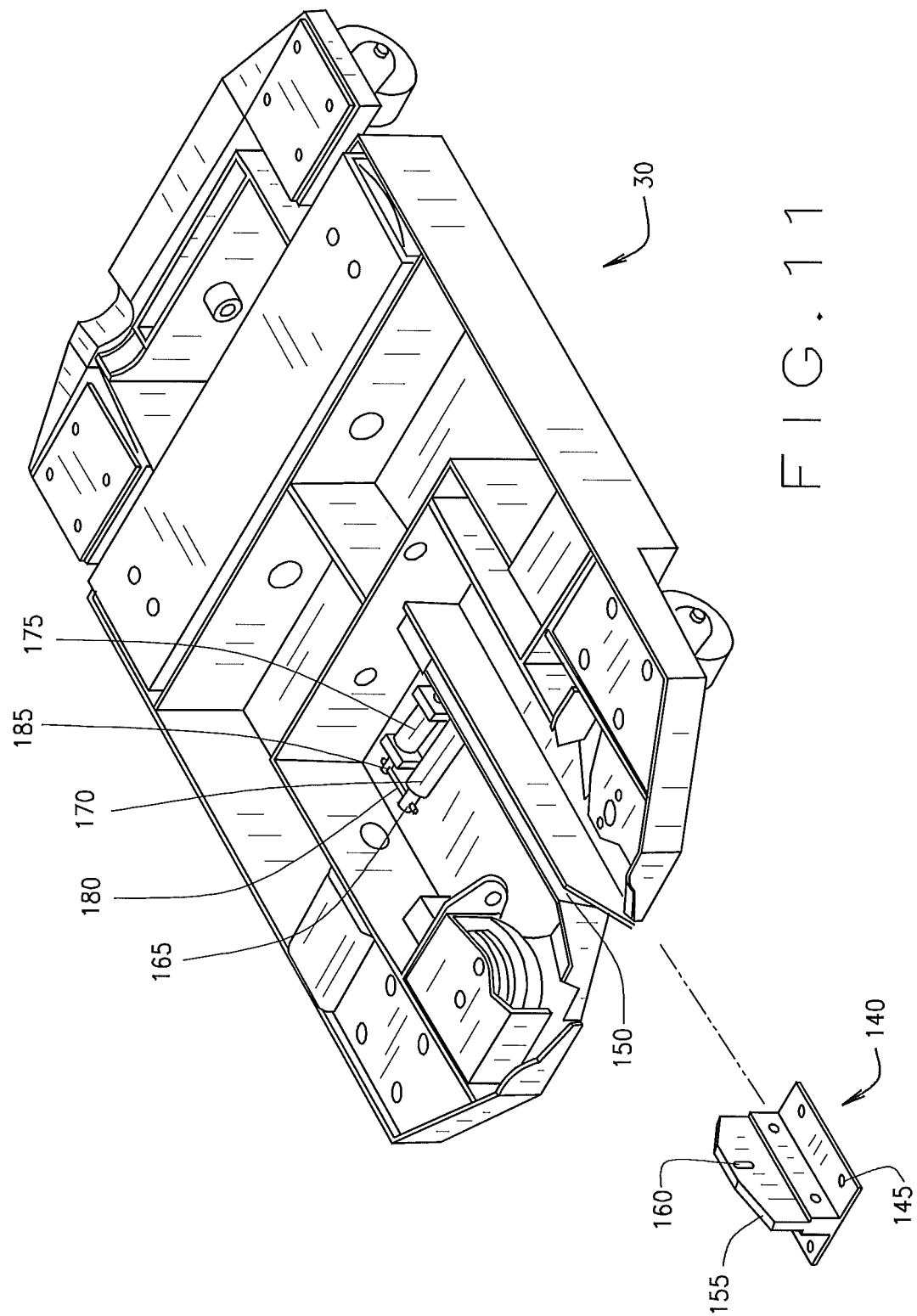
FIG. 11 illustrates an exploded view of a support frame member aligned for being received by a cart base member.

Cart 10 may be transported within a truck or other transportation means for transporting the cart 10 and highly sensitive equipment such as device 15. FIG. 11 illustrates a support frame member 140 receiving cart base member 30, which when used functionally may include a plurality of components and device 15 mounted thereon. Support frame member 140 is illustrated as an isolated component in FIG. 11, but in operation, it may be selectively mounted to the floor of a truck trailer, storage warehouse or other surface where carts 10 and highly sensitive equipment associated therewith is stored. Support frame member 140 includes a plurality of through holes 145 for receiving bolts for attaching the frame member 140 to a floor surface. Other means of securely attaching the support frame member 140 are contemplated herein.

A channel 150 extends through the front portion of cart base member 30 of a width sufficient for receiving a ridge 155 of the frame member 140. As such when the cart base member 30 and its components associated therewith are being transported, a means of securing the cart 10 and device 15 is provided. When the cart base member 30 approaches frame member 140, channel 150 receives ridge 155 of frame member 140. Frame member 140 may slide rearwardly into the channel 150 until it abuts the cart base member 30 where the channel 150 stops (not illustrated). When frame member 140 is abutting the end portion of channel 150, receiving eyelet 160 of frame member 140 is in substantial alignment with a pin 165 housed within a barrel cylinder 170. The pin 165 extends therethrough the cylinder 170 and has a friction fit within the cylinder 170 such that the pin 165 may slide within cylinder 170 when a force is applied to it, but the pin 165 does not slide within cylinder 170 if a force is not applied to it. Typically the pin 165 is controlled via a powered mechanism discussed herein below.

Figure 12:
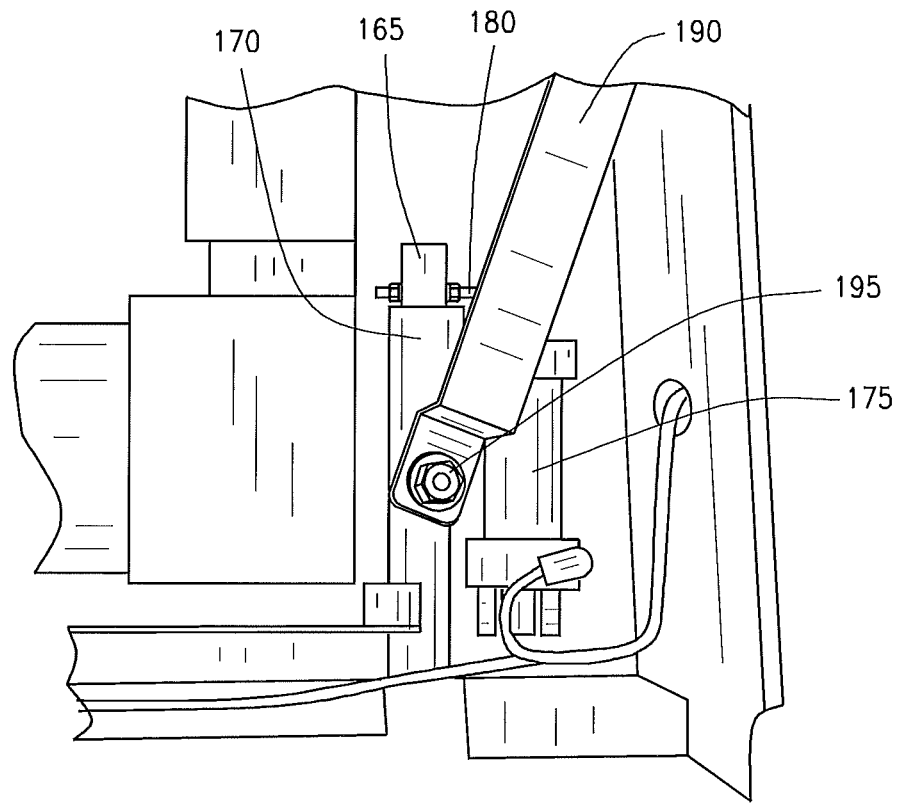
FIG. 12 illustrates an enlarged partial top plan view of a pin and manual release lever of the cart base member of FIG. 11.
Figure 13:
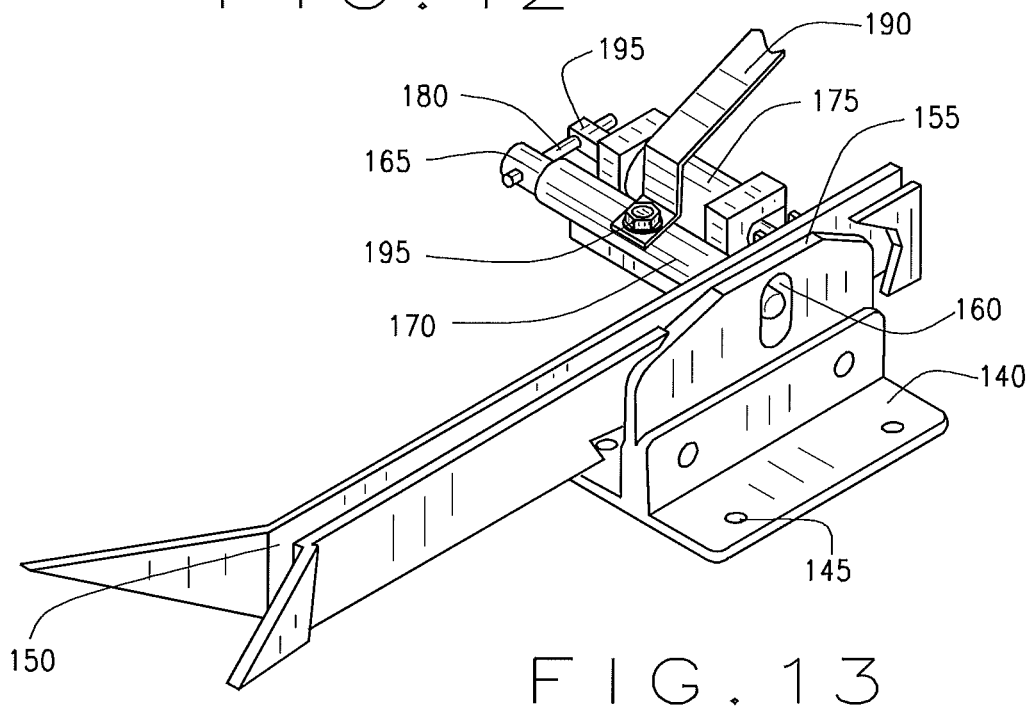
FIG. 13 illustrates a partial perspective view of the pin and manual release lever of the cart base member when selectively engaged with the support frame member.

FIGS. 12 and 13, along with FIG. 11 best illustrate the powered mechanism. A pneumatic actuator 175 located adjacent the cylinder 170 and associated therewith is located within cart base member 30. Pneumatic actuator 175 may be controlled via electronics and air supply means associated with actuator 175 and not illustrated in the figures provided. Pneumatic actuator 175 is in mechanical communication with pin 165 via attachment rod 180. When the pneumatic actuator 175 is activated via the aforementioned electronics and air supply means, air is injected into the actuator 175 which drives a piston to compress a spring contained therein actuator 175. When the spring is compressed, rod 185 associated with actuator 175 and connected with attachment rod 180 is forced outwardly. This outward force is consequently applied to pin 165 within cylinder 170. As a result, pin 165 is further removed from eyelet 160. The manner by which the actuator 175 functions is known in the art, and the actuator 175 and the components contained therein are commercially available.

Thus the pin 165 may be power-activated to be inserted into eyelet 160 in order to be secured to frame member 140 and consequently a floor surface, or it may be power-activated in order to be removed from eyelet 160 to release the pin 165 from the eyelet 160 and consequently the floor surface. The locking mechanism formed by the pin 165 and eyelet 160 may be used in loading and unloading carts 10 including highly sensitive equipment. In alternative embodiments the powered mechanism described above may not be pneumatic and may be otherwise hydraulically, mechanically, or otherwise controlled.

In a typical scenario, the pin 165 may engage the frame member 140 via eyelet 160 or disengage therefrom via the powered mechanism described above. Yet, in a scenario where power fails, a manual release mechanism for releasing the pin 165 from eyelet 160 is herein provided. A handle 190, a portion of which is illustrated in FIGS. 12 and 13, may further be attached to the cylinder 170. Handle 190 may be attached to the cylinder 170 by a bolt 195. At its other end, handle 190 may be releasably attached to a side portion of the cart base member 30 such that when the manual release mechanism is not needed, handle 190 is out of the way. Handle 190 may be attached to a side portion of the cart base member 30. The bolt 195 extends downwardly through cylinder 170 where it is further attached to pin 165.

In operation, in the event of a power failure or other event necessitating the manual release of a cart 10, handle 190 may be unattached from the side portion of cart base member 30. Handle 190 may then be turned and pulled in a forward direction, in the direction away from aperture 160 of frame member 140. When the handle 190 is pulled away from the aperture 160, bolt 195 attached to pin 165 causes pin 165 to be pulled away as well. It should be noted that cylinder 170 including pin 165 therein also is pulled away in the direction of the applied force. As a result, pin 165 may be removed from aperture 160 and frame member 140, allowing cart 10 to be disengaged from frame member 140 and thus being removable therefrom.

As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A cart for transporting highly sensitive equipment comprising:
    a cart base member for supporting said highly sensitive equipment and for allowing rolling movement of said cart relative to a floor surface;
    a rotary swivel bearing attached to said cart base member;
    a mounting plate configured for receiving and securing said highly sensitive equipment thereon attached to said rotary swivel bearing, wherein said rotary swivel bearing functionally rotates said mounting plate;
    a locking mechanism attached to said cart base member, said locking mechanism when in a closed position preventing the rotational movement of the mounting plate; and
    wherein the rotary swivel bearing is attached to the cart base member via a slotted block contained within the cart base member.

2. The cart of claim 1 wherein the rotary swivel bearing includes an upper plate and a lower plate, the upper plate able to be rotated while the lower plate remains in a fixed position.

3. The cart of claim 1 wherein the locking mechanism is a control handle.

4. The cart of claim 1 wherein the slotted block includes upward extending slots at end portions of the slotted block.

5. The cart of claim 4 wherein the cart base member includes inwardly extending lips, the lips being received and contained within the slots of the slotted block.

6. The cart of claim 1 wherein the rotary swivel bearing includes an upper plate and a lower plate, the lower plate able to be rotated, and further causing the upper plate to be rotated.

7. A cart for transporting highly sensitive equipment comprising:
    a cart base member for supporting said highly sensitive equipment and for allowing rolling movement of said cart relative to a floor surface;
    a rotary swivel bearing attached to said cart base member;
    a mounting plate configured for receiving and securing said highly sensitive equipment thereon attached to said rotary swivel bearing, wherein said rotary swivel bearing functionally rotates said mounting plate;
    a locking mechanism attached to said cart base member, said locking mechanism when in a closed position preventing the rotational movement of the mounting plate;
    wherein the rotary swivel bearing includes an upper plate and a lower plate, the upper plate able to be rotated while the lower plate remains in a fixed position; and
    wherein said cart base member includes a plurality of inflatable air bladders.

8. The cart of claim 7 wherein the cart includes a circular plate mounted to the upper plate of the rotary swivel bearing and to an underside of the mounting plate and a roller plate including a plurality of rollers, said roller plate positioned and located below the mounting plate such that when the air bladders are deflated, the mounting plate is in contact with the plurality of rollers of the roller plate.

9. A cart for transporting highly sensitive equipment comprising:

a cart base member for supporting said highly sensitive equipment and for allowing rolling movement of said cart relative to a floor surface;

a rotary swivel bearing attached to said cart base member;

a mounting plate configured for receiving and securing said highly sensitive equipment thereon attached to said rotary swivel bearing, wherein said rotary swivel bearing functionally rotates said mounting plate;

a locking mechanism attached to said cart base member, said locking mechanism when in a closed position preventing the rotational movement of the mounting plate; and wherein the cart base member includes a handle attached to a pin for selective manual removal from an aperture of a frame member mounted to a floor surface.

10. A system for transporting highly sensitive equipment comprising:
  a cart comprising:
    a cart base member;
    a rotary swivel bearing attached to said cart base member;
    a mounting plate attached to said rotary swivel bearing, said mounting plate configured for receiving and securing highly sensitive equipment thereon; and
    a locking mechanism attached to said cart base member;
  an asymmetric piece of highly sensitive equipment mounted to said mounting plate; and
  a support frame member mounted to a floor surface for securing said cart, said support frame member comprising an aperture extending therethrough, and wherein the cart base member includes a channel for receiving the support frame member therein.

11. The system of claim 10 wherein the cart base member includes a handle attached to a pin, and wherein the aperture of the support frame member is in substantial alignment with the pin when the support frame member is received by the channel of the cart base member.

12. The system of claim 11 wherein when the handle is manually pulled outwardly, the pin is removed from the aperture of the support frame member.

13. A method for rotating a mounting plate of a cart for mounting highly sensitive equipment thereon, the method comprising the steps of:
  deflating air bladders contained within a cart base member of the cart;
  releasing a control handle from attachment with a bracket upwardly extending from said mounting plate;
  pulling said control handle away from said mounting plate such that it hingedly rotates away therefrom; and
  rotating said mounting plate such that it operatively rotates via its attachment with a rotary swiveling bearing.

* * * * *